United States Patent [19]

Sherman

[11] Patent Number: 4,887,596

[45] Date of Patent: Dec. 19, 1989

[54] OPEN BACKED PEDICLE SCREW

[75] Inventor: Michael Sherman, King of Prussia, Pa.

[73] Assignee: Synthes (U.S.A.), Paoli, Pa.

[21] Appl. No.: 163,278

[22] Filed: Mar. 2, 1988

[51] Int. Cl.⁴ .............................................. A61F 5/04
[52] U.S. Cl. ..................................... 606/61; 403/235; 606/72; 606/73
[58] Field of Search ................. 47/92 YM, 69, 92 YL, 47/92 R, 92 ZZ, 92 ZW; 403/234–237, 362

[56] References Cited

U.S. PATENT DOCUMENTS

| | | | |
|---|---|---|---|
| 529,271 | 11/1894 | Hute | 403/235 |
| 1,798,572 | 3/1931 | Welton | 403/236 |
| 2,774,350 | 12/1956 | Cleveland, Jr. . | |
| 3,306,585 | 2/1967 | Blum | 403/234 |
| 3,865,105 | 2/1975 | Lode . | |
| 3,877,825 | 4/1975 | Roux | 403/237 |
| 3,997,138 | 12/1976 | Crock et al. . | |
| 4,404,967 | 9/1983 | Bacal et al. . | |
| 4,445,513 | 5/1984 | Ulrich et al. . | |
| 4,567,884 | 2/1986 | Edwards . | |
| 4,569,338 | 2/1986 | Edwards . | |
| 4,611,580 | 9/1986 | Wu | 128/69 |
| 4,641,636 | 2/1987 | Cotrel . | |
| 4,648,388 | 3/1987 | Steffee . | |
| 4,693,240 | 9/1987 | Evans . | |

FOREIGN PATENT DOCUMENTS 2649042 8/1978 Fed. Rep. of Germany .
3439795 10/1985 Fed. Rep. of Germany .

OTHER PUBLICATIONS

Three pages showing nine drawings of Spinal Fixation Assemblies.
Synthes Bulletin SIF-1-8/87, Date is 1987.

*Primary Examiner*—Richard J. Johnson
*Assistant Examiner*—Charles H. Sam
*Attorney, Agent, or Firm*—Davis Hoxie Faithfull & Hapgood

[57] ABSTRACT

A pedicle screw for use in internal fixation of the spine comprising a shaft threaded at one end for insertion into a bone and, at the other end, having a yoke for receiving a rod, said yoke having a cusp adapted to bear against the rod and means for clamping the rod against the cusp, while permitting adjustment of the angle between said rod and said yoke.

8 Claims, 2 Drawing Sheets

OPEN BACKED PEDICLE SCREW

This invention relates to a pedicle screw for use in internal fixation of the spine and in particular to a pedicle screw which is compact, adjustable and capable of being applied to adjacent vertebrae.

Internal spinal fixation systems are used in the treatment of spinal fractures and to correct spinal deformities. In general such systems involve screws having long shafts, which are inserted into the pedicles and which are then clamped to rods or plates which run roughly parallel to the spine. The screws serve as anchors on the spine and by adjusting the position of the shafts of the screw relative to the rods or plates, the spine, or a section thereof, can be immobilized in the desired configuration.

The manner in which the pedicle screws are attached to the rods has been the subject of much thought and there are a wide variety of clamps and brackets for achieving this end. However, prior proposals have involved devices which are complicated in construction and excessively bulky; so much so that it has been difficult if not impossible to attach the rod/screw assembly to adjacent vertebrae. Moreover, with many devices the rod must be secured to one or more screws before all the screws are inserted. In some devices the rod is threaded making a change of relative position of the rod and the screws awkward.

The present invention provides a pedicle screw which is readily adjustable in a variety of dimensions, which is compact enough to be used on adjacent vertebrae and which can receive rods after the screws have been placed in the spine and permit adjustment.

In accordance with the invention, a pedicle screw comprises a shaft, threaded at one end for insertion into bone and clamping means comprising a yoke or trough adapted to receive a rod at the other end. The interior of the forward end of the yoke is preferably shaped to form a projection, most preferably in the form of a cusp whose edge is adapted to bear against an inserted rod, and means in the yoke for clamping an inserted rod against the cusp.

Preferably the clamping means is a block or panel, slidingly mounted in the yoke and having screw means for pressing the rod against the cusp or projection. The screw means preferably comprises two screws, one on either side of the cusp or projection so that the rod can be tilted by advancing one screw or the other.

The yoke is preferably provided with grooves and the block has matching grooves which dovetail with the grooves in the yoke allowing the block to slide in the yoke. A socket and a matching projection are preferably provided in the grooves of the yoke and block so that when the block is tightly clamped against a rod inserted in the yoke the block is prevented from sliding in the yoke.

The invention further comprises a spinal fixation assembly comprising a pedicle screw as described, in combination with a rod for insertion in the yoke of the screw.

The invention will be described more fully in connection with the accompanying drawings in which.

Figure 1:
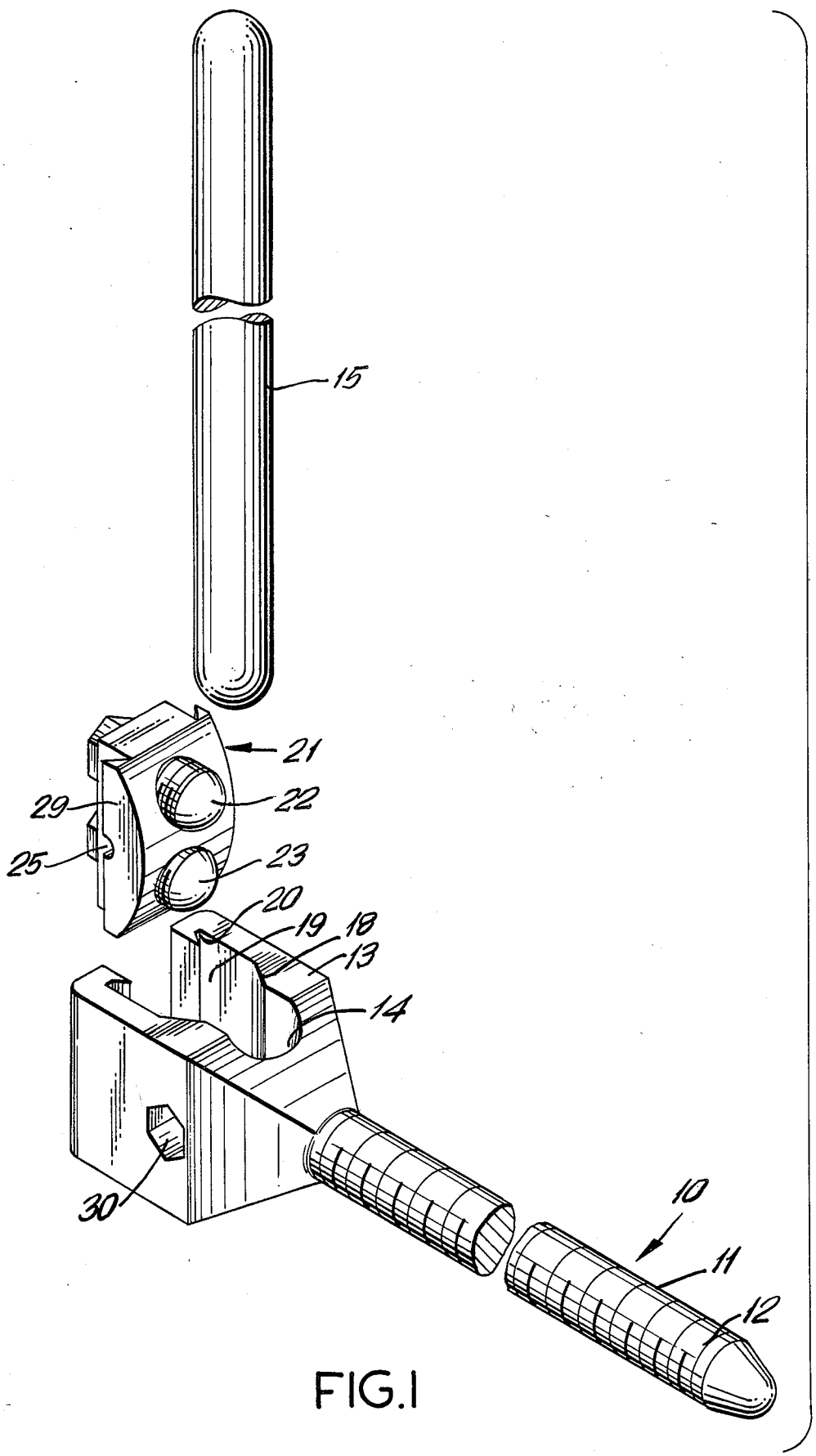
FIG. 1 is an exploded perspective view of a spinal fixation assembly using a pedicle screw according to the invention.
Figure 2:
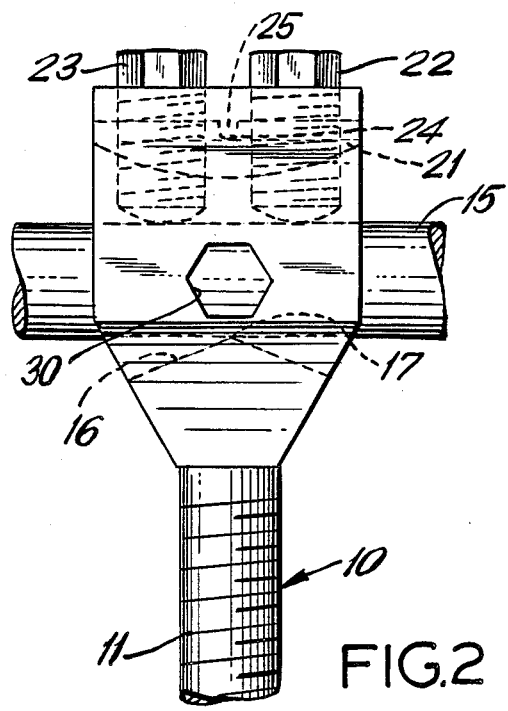
FIG. 2 is a side view of a pedicle screw according to the invention.
Figure 4:
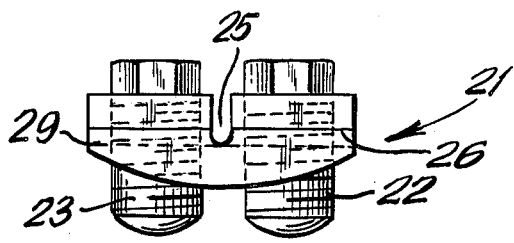
FIG. 4 is a view in side elevation showing details of the block shown in FIGS. 1, 2 and 3.
Figure 5:
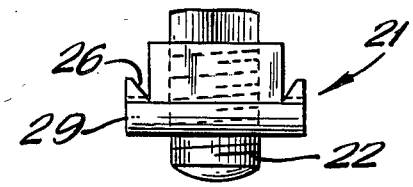
FIG. 5 is an end view of the block of FIG. 4 showing the dovetail slot for engagement with the yoke.

Referring to the drawings, FIG. 1 shows a screw according to the invention. The screw, indicated generally as 10, comprises a shaft 11 which is threaded at one end as at 12 and preferably somewhat pointed for introduction into the bone. At the opposite end is a yoke or trough 13. The forward end of the yoke is curved as at 14 to receive a rod 15. The rod 15 may be smooth, i.e., unthreaded. As shown more clearly in FIGS. 2 and 3, the front inside wall 16 of the yoke is tapered inwardly to form a cusp or projection 17 against which the rod 15 can bear. The side walls 18 of the yoke are provided with grooves or slots 19 having rear undercut portions 20, for receiving a panel or block 21. As shown in FIGS. 4 and 5, the block 21 has lands 29 with matching undercut portions 26 which form a dovetail joint with the undercut portions of the yoke.

Figure 3:
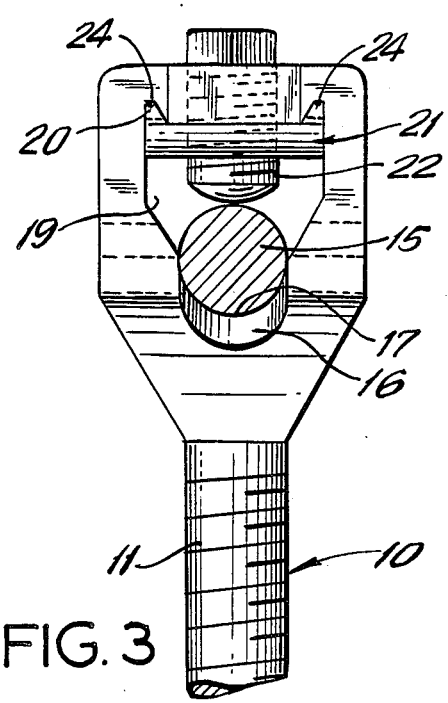
FIG. 3 is an end view of the screw of FIG. 2.

The block 21 is provided with two set screws 22 and 23 which, as shown in FIG. 3, can be advanced through the block to contact the rod 15, pressing it against the cusp 17 formed in the forward inner surface of the yoke. The outer ends of the set screws 22, 23 may be given hexagonal heads so that they may be operated by a suitable wrench. The thickness of the block 21 is considerably less than the depth of the yoke 19, so that it will fit loosely in the yoke. However, when the screws 22, 23 are advanced to bear against an inserted rod, as shown in FIG. 3, the block is forced back so that the undercut portions 26 of the lands 29 engage the undercut portions 20 of the yoke.

The interior of the undercut portions 20 of the slots 19 may be provided with a small projection 24 (FIGS. 2 and 3) and a matching socket 25 is provided in the block 21 so that when the screws 22, 23 are advanced and press against a rod, forcing the block back against the rear part of the slots 19, the projections 24 will seat in sockets 25 preventing sliding of the block in the socket.

In use the screw may be inserted into the pedicle using Kirschner wires to provide guide holes according to conventional teaching. Sockets 30 may be provided in the side walls of the screw yoke for aid in manipulating the screw. After two or more of the screws have been positioned at the points desired, a rod may be inserted through the open rear ends of the yokes of the screws. The blocks 21 are then dropped into the slots 19 and the set screws 22, 23 tightened. Since the contact between the rod and the inside of the yoke is at the cusp 17, by advancing one screw or the other the rod may be tilted relative to the screws. This may be used, inter alia, to bring the spine itself to a desired alignment, to correct spinal deformities.

Figure 6:
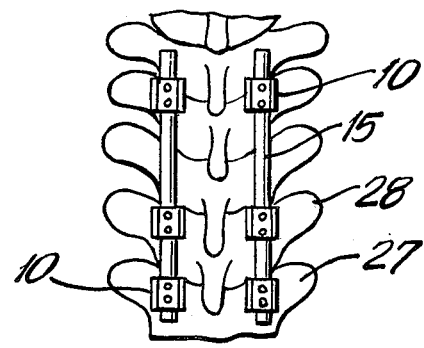
FIG. 6 is a schematic posterior view of a portion of a vertebral column showing the use of pedicle screws in spinal fixation assemblies according to the invention.

FIG. 6 shows a sequence of thoracic vertebrae to which two fixation rods using pedicle screws according to the invention have been applied. The lateral dimensions of the yoke end of the screw may be quite small; on the order of 12×12 mm, for example. It is therefore possible, as shown in FIG. 6, to insert screws according to the invention in adjacent vertebrae 27, 28 without interference. Moreover, because the angle between the screw and rod can be adjusted by balancing the two set screws it is possible to adjust the angle of the rod after it is in position with great ease.

What is claimed is:

1. A pedicle screw comprising a shaft having a forward end, a rear end and a longitudinal axis, said forward end being threaded for insertion into a bone and said rear end having a yoke attached thereto, the interior wall of said yoke nearest the shaft having a projection comprising two tapered walls forming an edge, said edge of said projection being adapted to bear against a rod inserted into the yoke, and means in said yoke for clamping a rod inserted in said yoke against said edge.

2. The pedicle screw claimed in claim 1 and comprising a block, means for slidingly mounting said block in said yoke and means on said block for clamping a rod inserted in the yoke at a variety of angles to the longitudinal axis of the shaft.

3. The pedicle screw claimed in claim 1 and comprising grooves in the sides of said yoke, a block having lands matching the grooves in the sides of the yoke for slidingly mounting the block in the yoke and screw means in the block for pressing a rod inserted in the yoke against the edge of the projection.

4. The pedicle screw claimed in claim 3 wherein the screw means comprises two set screws, adapted to bear against said rod on opposite sides of the edge of the projection.

5. The pedicle screw claimed in claim 3 wherein the grooves in the yoke and the lands in the block have undercut portions which dovetail with one another.

6. The pedicle screw claimed in claim 3 and comprising means in said undercut portions for suppressing relative movement between said block and said yoke.

7. A pedicle screw comprising a shaft and clamping means on said shaft for clamping said shaft to a rod running transversely to the axis of the shaft, said clamping means comprising a yoke on an end of said shaft, an interior wall of said yoke having inwardly extending fulcrum means for contacting a rod inserted in said yoke, a panel removably mounted in said yoke, and means in said panel for pressing a rod inserted in said yoke against said fulcrum means.

8. The pedicle screw claimed in claim 7 wherein said panel has screws adapted to be advanced into said yoke on either side said fulcrum means, for tilting a rod inserted in the yoke relative to the axis of the shaft.

* * * * *